(12) United States Patent
Yoda

(10) Patent No.: US 6,298,114 B1
(45) Date of Patent: Oct. 2, 2001

(54) X-RAY MAMMOGRAPHY APPARATUS

(75) Inventor: Kiyoshi Yoda, Hyogo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 08/386,569

(22) Filed: Feb. 10, 1995

(30) Foreign Application Priority Data

May 11, 1994 (JP) .................................................. 6-097634

(51) Int. Cl.[7] ....................................................... A61B 6/04
(52) U.S. Cl. ................................................................ 378/37
(58) Field of Search ................................................. 378/37

(56) References Cited

U.S. PATENT DOCUMENTS

| | | | |
|---|---|---|---|
| 3,965,357 | * 6/1976 | Hounsfield | 378/18 |
| 3,973,126 | * 8/1976 | Redington et al. | 378/37 |
| 4,119,841 | * 10/1978 | Jantsch et al. | 378/19 |
| 4,206,763 | * 6/1980 | Pedersen | 128/660 |
| 4,485,481 | * 11/1984 | Takano | 378/19 |
| 4,905,150 | 2/1990 | Aichinger et al. | |
| 4,926,453 | 5/1990 | Toniolo | |
| 5,018,176 | 5/1991 | Romeas et al. | |
| 5,050,197 | 9/1991 | Virta et al. | |
| 5,078,142 | * 1/1992 | Siczek et al. | 378/37 |
| 5,148,460 | 9/1992 | Aichinger | |
| 5,150,393 | 9/1992 | Aichinger et al. | |
| 5,164,976 | 11/1992 | Scheid et al. | |
| 5,289,520 | 2/1994 | Pellegrino et al. | |

OTHER PUBLICATIONS

P.E. Sijens et al., "NMR Spectroscopy of human breast tumors before and after radiotherapy, using a 1.5 T MRI system," MR research note, Selected Abstracts submitted to the 6th SMRM 1987, Phillips Medical Systems, Documentation No. 4535 983 00655 (Aug., 1987).

* cited by examiner

Primary Examiner—Craig E. Church
(74) Attorney, Agent, or Firm—McDermott, Will & Emery

(57) ABSTRACT

An X-ray mammography apparatus for more reliable and less painful diagnosis, by providing means for elongating the breast using gravity or force of suction. In one form, the patient is horizontally positioned on a bed having a hole for elongating the breast. An X-ray source and a film table are located under the bed, thereby allowing an X-ray beam going horizontally through the patient's breast. An advantage is that a cancer near the chest wall can be more reliably detected.

13 Claims, 16 Drawing Sheets

PRIOR ART

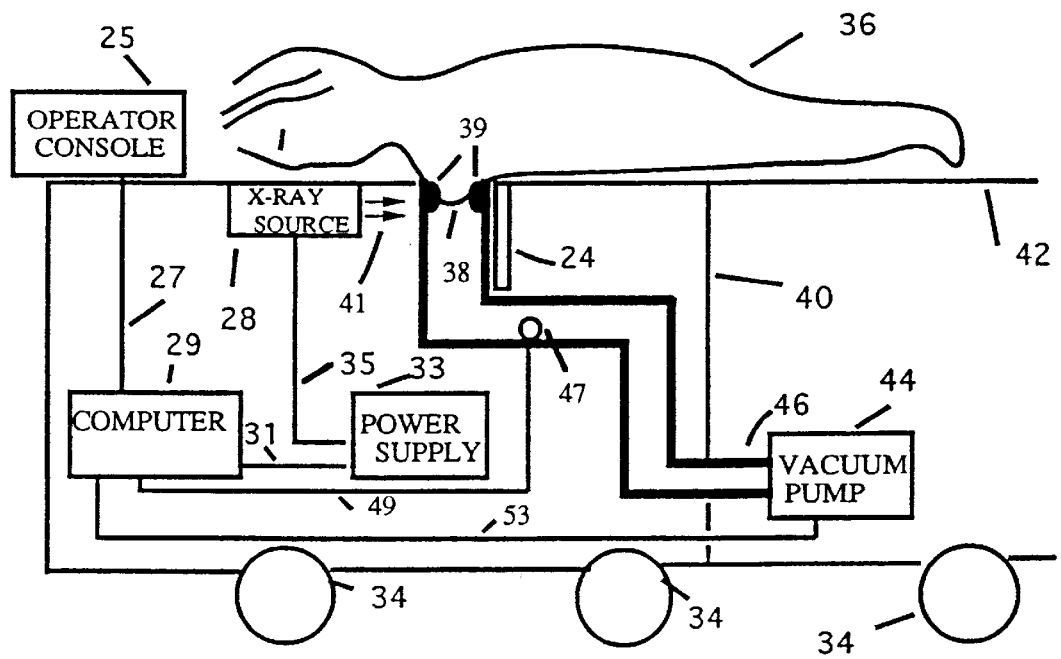
FIG. 7
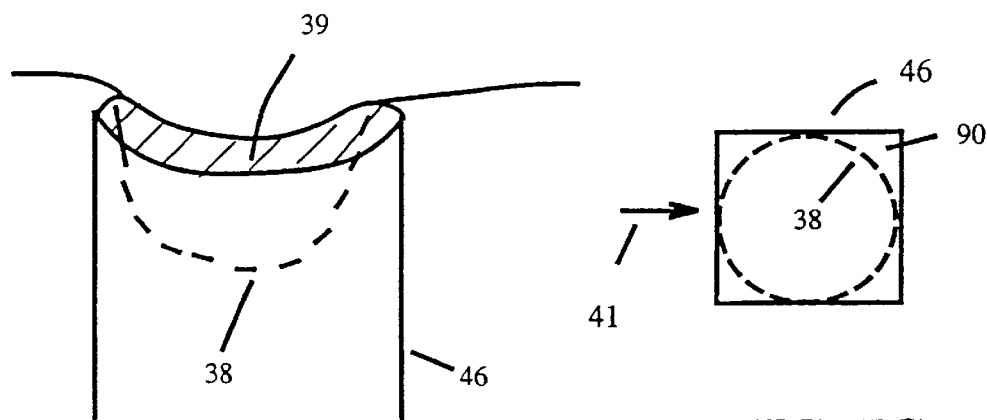
FIG. 7A
FIG. 7C

X-RAY MAMMOGRAPHY APPARATUS

TECHNICAL FIELD

The present invention relates generally to medical X-ray systems, and more particularly, to an improved X-ray mammography apparatus for detecting breast cancer or other breast diseases.

BACKGROUND ART

Mammography machines are used for X-ray examination of the female human breast (the milk-producing organ) to detect cancer or other growths. A typical machine is described in detail in U.S. Pat. No. 5,164,976, the disclosure of which is hereby incorporated by reference. FIG. 1 depicts a conventional mammography machine shown in the above United States Patent. The mammography machine includes an operator control unit and X-ray generator portion indicated at 20. The portion 20 incorporates the control electronics for the machine as well as the power supply for an X-ray source. The machine portion indicated at 22 is sometimes referred as a C-arm assembly and includes a film table 24, an overlaying compression paddle 26 and an X-ray source 28. The C-arm assembly may be rotatable about a horizontal axis 30 for obtaining different angular images. A radiation shield 32 isolates the operator control area adjacent portion 30 from the patient area adjacent film table 24. The C-arm 22 is vertically adjustable, in the position shown in FIG. 1, to accommodate date patients of different heights. The table 24 accepts standard X-ray film cassettes for image recording.

In conducting a mammography examination, a patient's breast is placed upon film table 24 and is compressed by compression paddle 26. The compression is required in order to have a substantially uniform density or thickness of the breast typically necessary to provide rather uniform X-ray image density characteristics. The reason is that the conventional X-ray films have relatively small dynamic ranges, and therefore the X-ray beam intensity must be within a certain small variation when reaching the film table 24. Otherwise, higher intensity area will be overexposed or lower intensity area will be underexposed depending on the exposure time.

The foregoing mammography machine includes many drawbacks. One of the most obvious ones is demonstrated in FIG. 2, wherein two cancer areas 80 and 82 are shown in a patient's breast 38. If the breast 38 is compressed by the compression paddle 26, the cancer area 82 moves toward the center of the field of view while the cancer area 80 moves out of the field of view. This means that there is a significant possibility that we cannot detect a cancer being located near the chest wall. Another disadvantage is that the compression procedures are often painful for patients having smaller breasts due to higher compression force.

DISCLOSURE OF THE INVENTION

A primary object of the invention is to provide a mammography machine that gives significantly higher cancer detectability near the chest wall.

Another object of the invention is to provide a mammography machine that gives less pain to a patient.

The above and other objects of the invention are satisfied, at least in part, by providing means for elongating the patient's breast by applying to the breast a tensile force.

In accordance with a preferred embodiment of the invention, means for elongating the breast using gravity is provided. Preferably, the patient is lain prone on a bed having a hole or cut area for elongating the breast. An X-ray source and an X-ray image detector are located under the bed, thereby allowing an X-ray beam going horizontally through the elongated breast.

According to one aspect of the invention, means for elongating the breast under force of suction such as by applying negative pressure is provided. Preferably, this configuration can be added to the system using gravity. In other words, the patient is lain prone on a bed having a hole for elongating the breast. An X-ray source and an X-ray image detector are located under the bed, thereby allowing an X-ray beam running horizontally through the breast. Furthermore, at least a part of the breast is covered by one end portion of a tube, wherein the internal pressure is controlled to be negative compared to the atmospheric pressure by operating a vacuum pump that is connected to the tube. The tube is made of an X-ray transparent material such as plastic.

According to another aspect of the invention, only the body portion above the chest is placed horizontally for elongating the breast using gravity. The elongation can be achieved by the gravity and the negative pressure at the same time.

According to still another aspect of the invention, a water reservoir is placed under the breast in order to provide almost the same X-ray attenuation with respect to the incoming X-ray beams even when avoiding the use of the compression paddle. Because the X-ray attenuation rate of the water is very close to that of human tissues, this configuration can reduce the dynamic range of the X-ray beam intensity on the X-ray film surface.

Alternatively, a semiconductor type X-ray image detector can be used for increasing the detector dynamic range, so that we can avoid using the compression paddle. A higher contrast X-ray film may also be used for increasing the detector dynamic range.

According to another aspect of the invention, means for elongating the breast using negative pressure can be provided without being prone. In this case, the patient can be vertically or uprightly positioned. Thus, we can use any conventional mammography apparatus by adding a tube and a vacuum pump. The tube is made of an X-ray transparent material such as plastic. One end of the tube covers at least a part of the breast while the other end being connected to the vacuum pump for applying the negative pressure to the breast.

Still other objects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of modifications in various obvious respects, all without departing from the invention. Consequently, the drawing and description are to be regarded as illustrative in nature, and not as restrictive.

BRIEF DESCRIPTION OF DRAWINGS

FIG. 7 is a diagram showing another example of mammography apparatus according to the present invention.

FIG. 7A is a diagram showing a tube that covers the breast that is used in FIG. 7.

FIG. 7C shows the cross sectional configuration of a water-carrying tube used in an embodiment of the invention.

BEST MODE FOR CARRYING OUT THE INVENTION

The invention is based in part on the realization that the patient's breast is elongated over an X-ray image detector using gravity or force of suction (such as by applying a negative pressure). This results in more reliable diagnosis for breast diseases such as breast cancer, because the cancer near the chest wall is more easily detectable.

Figure 3:
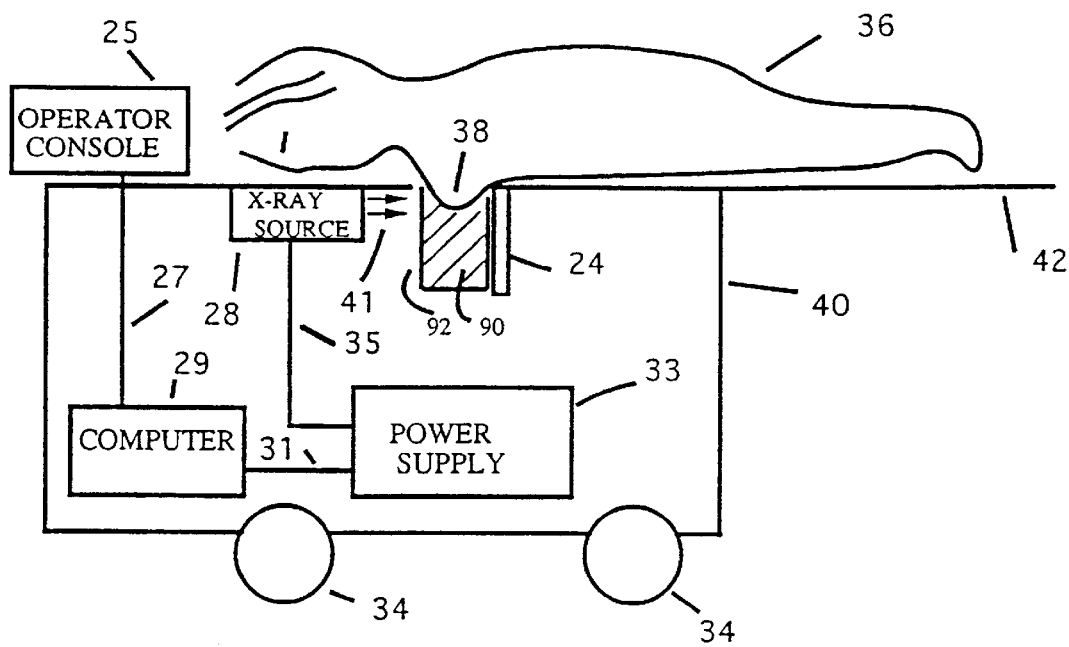
FIG. 3 is a diagram of a mammography apparatus in accordance with teaching the present invention.
Figure 3A:
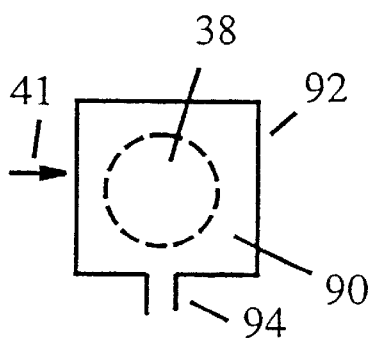
FIGS. 3A and 3B are diagrams of a water reservoir placed under a patient's breast being used in the mammography apparatus of FIG. 3.
Figure 3B:
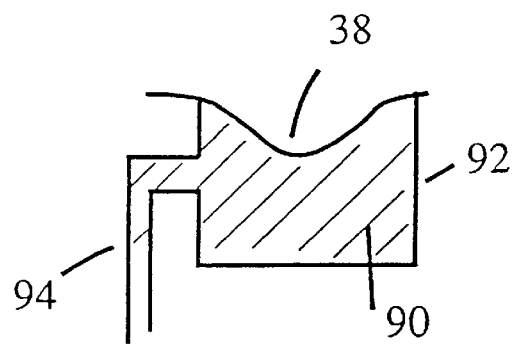

Reference is made to FIG. 3, wherein a patient 36 is positioned prone on a bed 42. The bed 42 has a hole for inserting the patient breast 38. An X-ray source 28 and an X-ray image detector means such as a conventional X-ray film table 24 are positioned under the bed 42, so that an X-ray beam 41 can be emitted horizontally toward the film table 24 through the breast 38. The film table contains standard X-ray film cassettes for detecting a mammography image. A water reservoir 92 being made of an X-ray transparent material such as plastic is placed under the bed and the breast 38 is placed into the reservoir 92. The reservoir contains water 90. FIG. 3A shows a top view of the reservoir 92, wherein the direction of the incoming X-ray beam 41, the rectangular cross-sectional shape of the reservoir 92, and the breast 38 are shown. There is also a pipe 94 being located on the side wall of the reservoir 94, whereby water is supplied to the reservoir 92. FIG. 3B shows a detailed side view of the reservoir 92. Because the total thickness of the breast and the water remains constant in the direction of the X-ray beam radiation, the variation of the beam intensity on the X-ray film surface can be reduced, thus avoiding local overexposure that possibly happens near the nipple position or underexposure that possibly happens near the chest wall position. This is achieved by the fact that the X-ray absorption rate of the breast tissue is nearly the same as that of water. The X-ray source 28 is connected to an X-ray power supply 33 through an electric cable 35. The power supply 33 is controlled by a computer 29 and an operator console 25, each of which is connected through an electric cable 31 or 27. The bed 42 is supported by an enclosure 40 that includes the X-ray source 28, film table 24, power supply 33, computer 29. The whole system can be moved on a floor with the aid of wheels 34. Elements except the water reservoir 92 and the bed 42 are conventional; 42 will be described later.

Figure 3C:
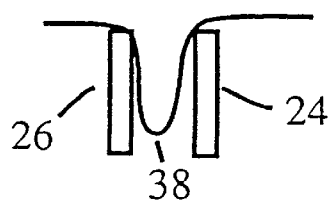
FIGS. 3C is a diagram of a different configuration being used in the mammography apparatus of FIG. 3.

FIG. 3C shows alternative configuration using the conventional compression paddle 26 that can move horizontally for applying proper pressure against breast 38. Because the breast is elongated by gravity downward, the cancer detectability near the chest wall can be maintained even when using the compression paddle.

Figure 4:
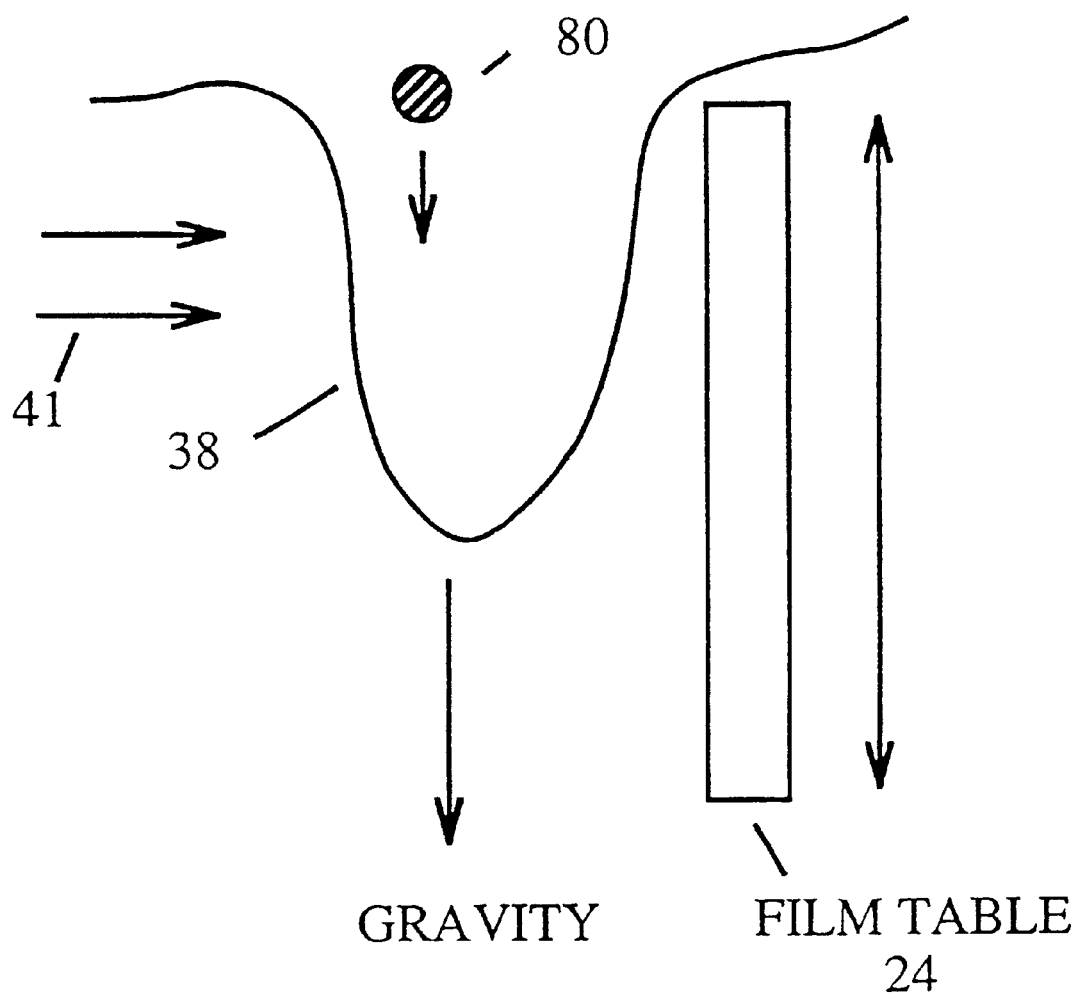
FIG. 4 is a diagram showing an advantage of the invented mammography machine.

FIG. 4 is a diagram showing an advantage of the invented mammography machine. The cancer area 80 near the chest wall moves downward because gravity is applied to the breast 38. This allows the cancer 80 to be detected on the film.

Figure 5:
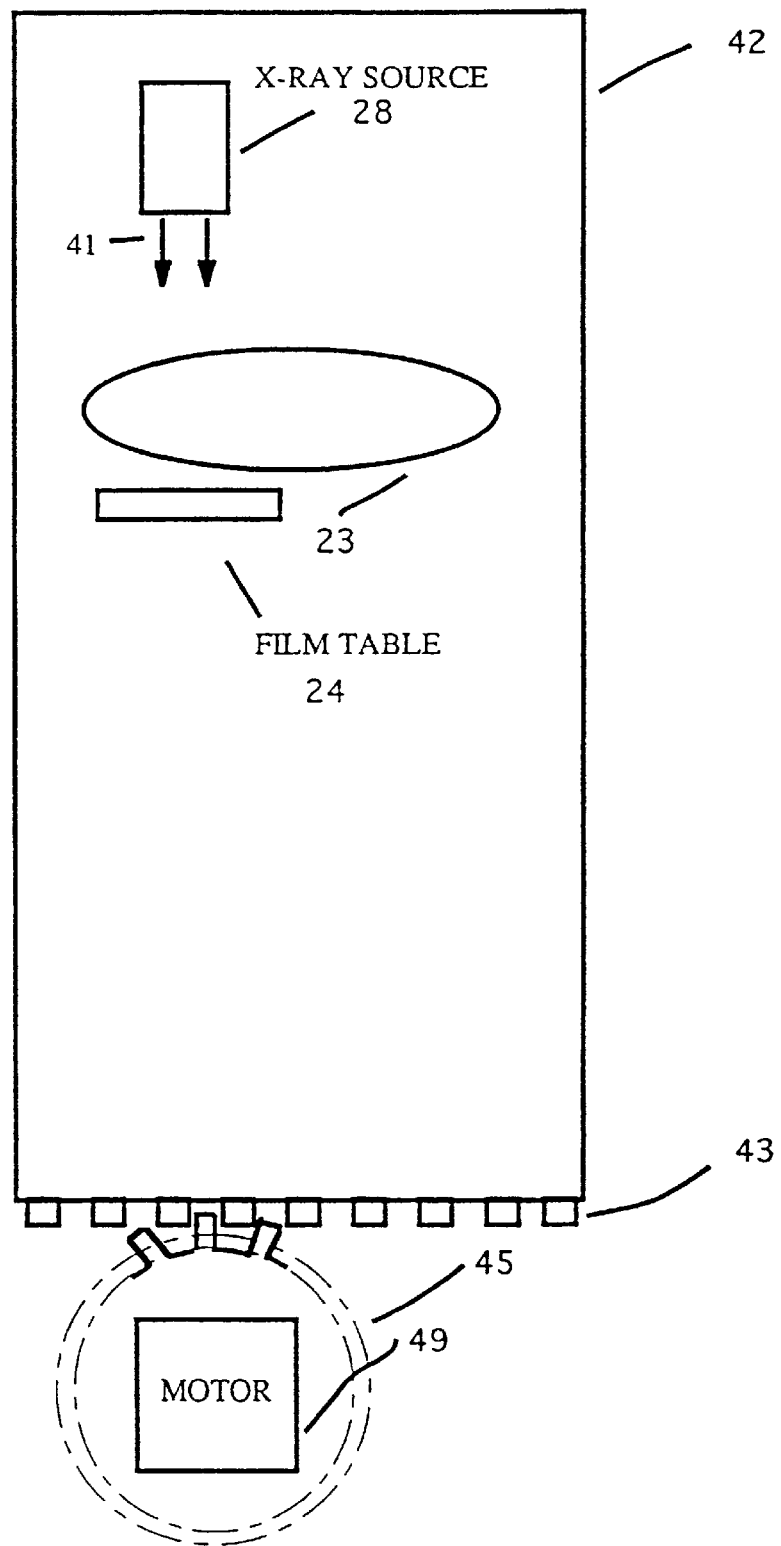
FIG. 5 is a diagram explaining sequence control mechanism for successive left and right breast imaging.

FIG. 5 is another diagram, a bed structure viewed from bottom, explaining a sequence control mechanism for successive left and right breast imaging. This is achieved by further providing a means for changing the spatial relationship between the breast-positioning means (such as the bed) and the X-ray generation and detection means. The bed 42 has a hole 23 for positioning left and right breasts. At one end of the bed 42, there are racks 43 being mechanically connected to a gear 45 being further connected to a rotary-motor 49. In operation, rotating motor 49 allows the bed 42 to move to the right or to the left. Because X-ray source 28 and film table 24 can be spatially fixed, the right and left breasts can be successively examined by this control mechanism. Other ways for moving the bed include linear- or rotary-type actuators utilizing air pressure or oil pressure. A linear motor can also be used instead of the rotary-motor 49.

Figure 6:
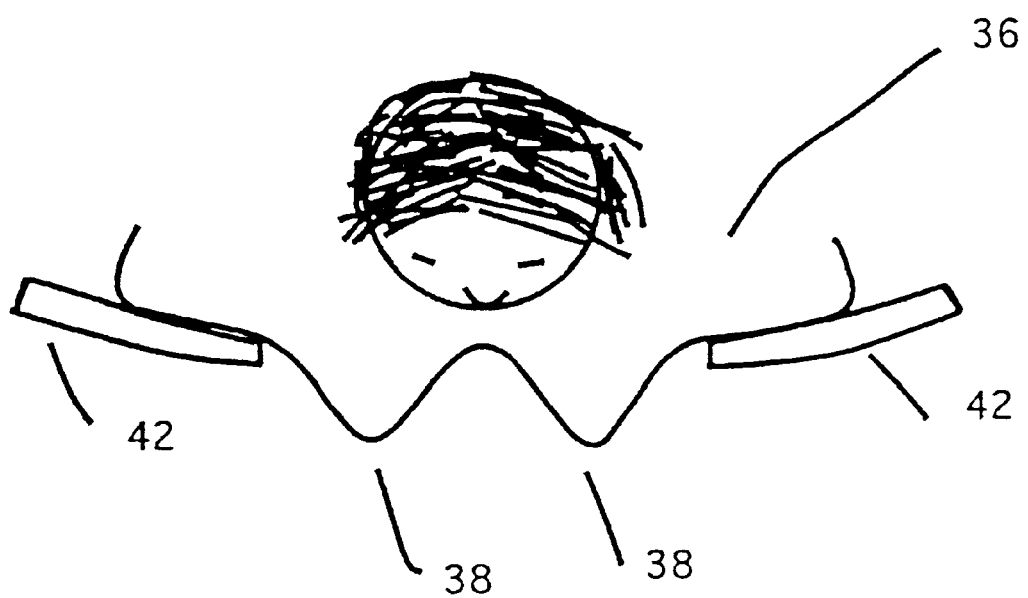
FIG. 6 is another diagram showing a preferred cross-sectional shape of the bed that practically matches with a patient body shape.

FIG. 6 indicates a preferred curved cross-sectional shape of the bed 42 in order to match the bed shape with the human body shape, thus maximizing imageable breast region and cancer detectability near the chest wall.

FIG. 7 depicts another embodiment to achieve this invention. The mammography machine in FIG. 7 is similar to that in FIG. 3; therefore, only different portions are explained hereinafter. A tube 46 running through enclosure 40 is positioned between the patient's breast and vacuum pump 44. Tube 46 contains a fluid such as air or water. There is a fluid seal 39 made of a rubber-like material between the breast and the tube end. The tube is made of an X-ray transparent material such as plastic. The inner pressure of the tube 46 is detected by a pressure sensor 47 and controlled by the computer 29 to avoid an excess negative pressure. Besides the operation of the machine in FIG. 3, the vacuum pump 44 makes the internal fluid pressure of tube 46 negative compared to the atmospheric pressure. Therefore, breast 38 is further elongated by means of the negative pressure. This further increases the cancer detectability in a wider chest wall area. In case of using water as the fluid in tube 46, the cross section of tube 46 is preferably rectangle (FIG. 7C). This provides the same effect as the water reservoir in FIG. 3, wherein the X-ray beams run parallel to the tube wall. As a result, the X-ray beam intensity on the film surface is practically uniform. This can avoid local overexposure or underexposure on the film even when using no compression paddle.

FIG. 7A is a detailed view of the breast 38 and the tube 46 interface. The fluid seal portion 39 is drawn by hatched lines.

Figure 7B:
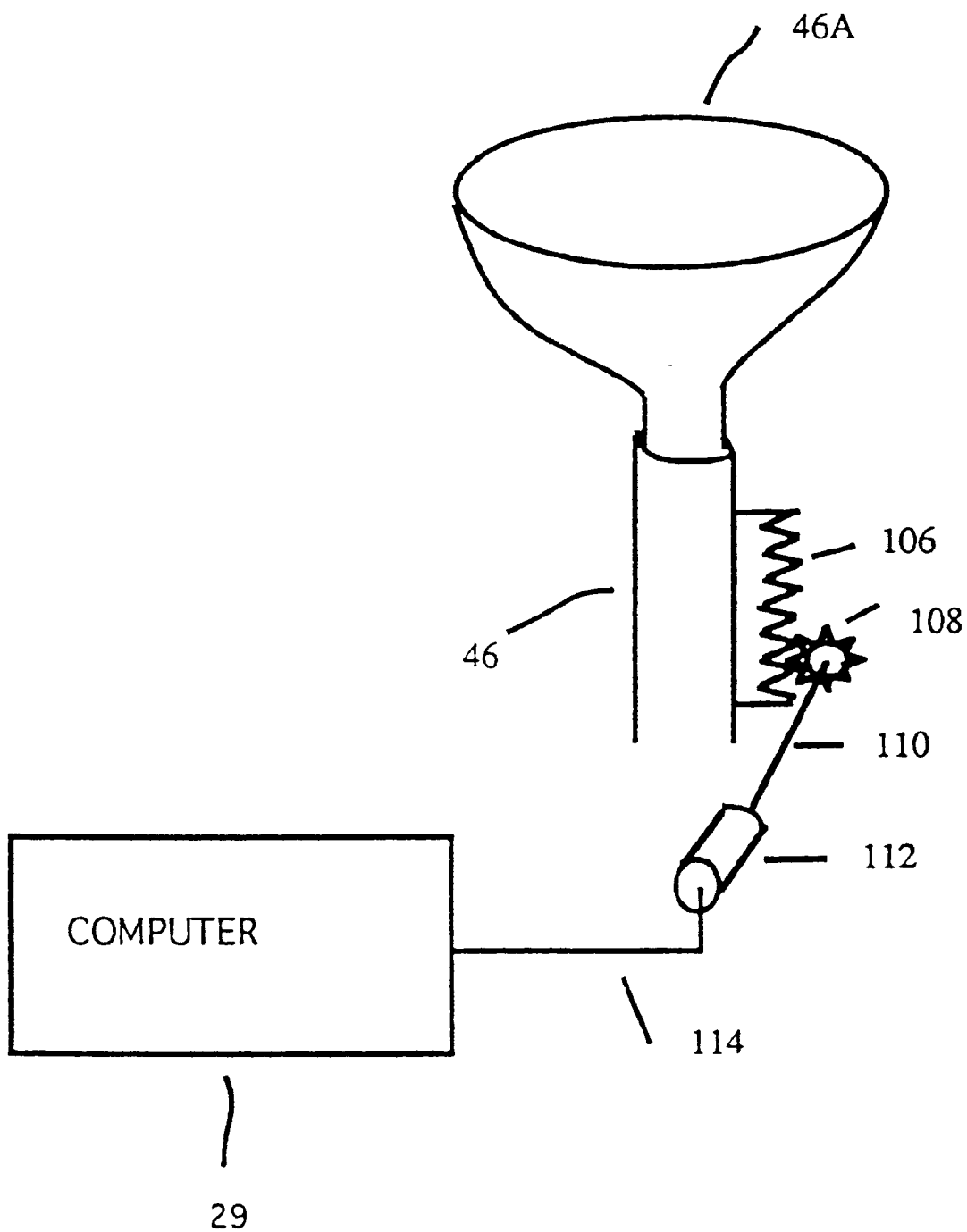
FIG. 7B is a different configuration showing a receptacle for covering the breast and a tube the other end of which is connected to the vacuum pump in FIG. 7.

FIG. 7B is a variation of the breast drawing configuration, wherein a bowl-shaped receptacle 46A is provided to cover a breast and connected to the tube 46. In this case, breast 38 can be further pulled down by moving receptacle 46A downward. This is achieved by a rack portion 106 attached on the wall of the tube 46, a wheelgear 108 connected to the rack 106, a rotating shaft 110 connecting the gear 108 to a motor 112, a control cable 114 for connecting the motor 112 to computer 29.

Although a tube 46 or receptacle 46A is depicted in the described embodiment, other configurations serving as a chamber for the breast can be adopted.

Figure 8:
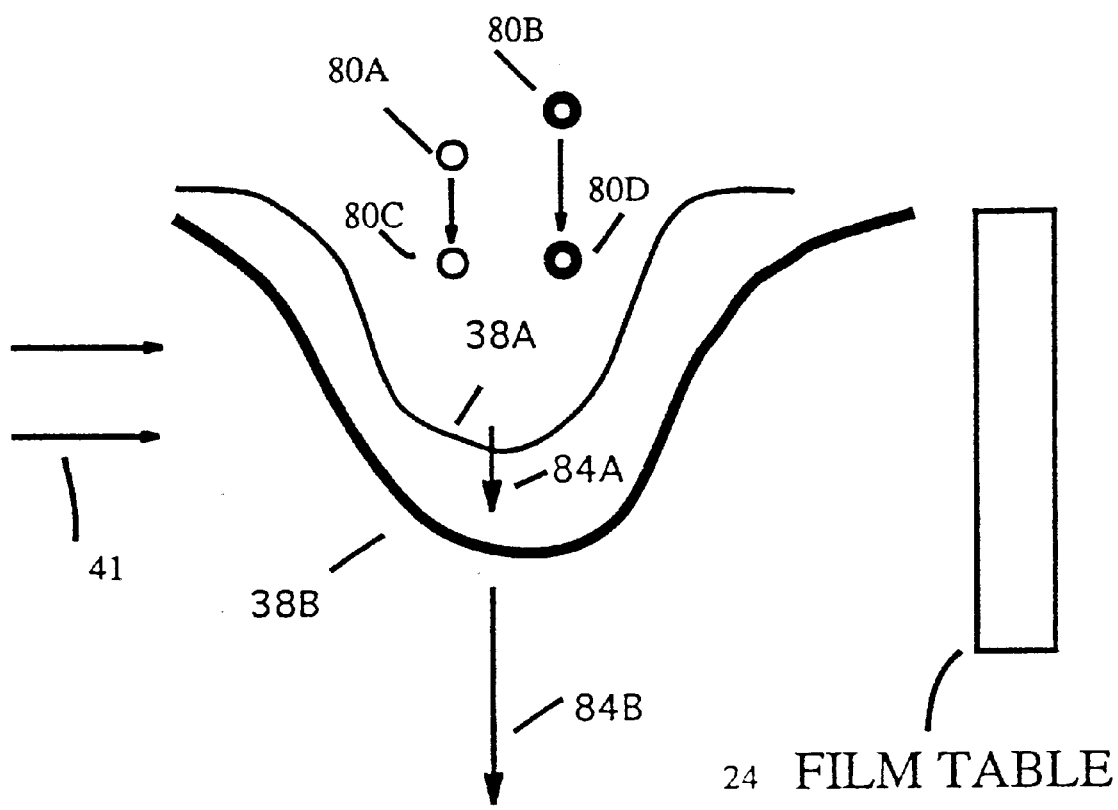
FIG. 8 is a diagram showing another advantage of mammography apparatus according to the present invention. The diagram shows two different elongating situation: elongation by only gravity (thin line) and elongation by both gravity and negative pressure (thick line).

FIG. 8 is a diagram showing another advantage of mammography apparatus according to the present invention. X-ray beams 41 are radiated on a film table 24 through a patient's breast. A breast 38A is elongated by only gravity 84A and a breast 38B is elongated by both gravity and force of suction 84B. A cancer 80A located near the chest wall moves downward to a position BOC due to the gravity 84A. By applying both the gravity and force of suction 84B, another cancer 80B located much deeper chest portion moves downward to a position 80D. Note that original positions 80A and 80B are out of the imageable region of the film table 24, while the positions 80C and 80D are inside the imageable region of the film table 24. By using both gravity and force of suction, cancer located in a deeper chest wall area can be detected.

Figure 9:
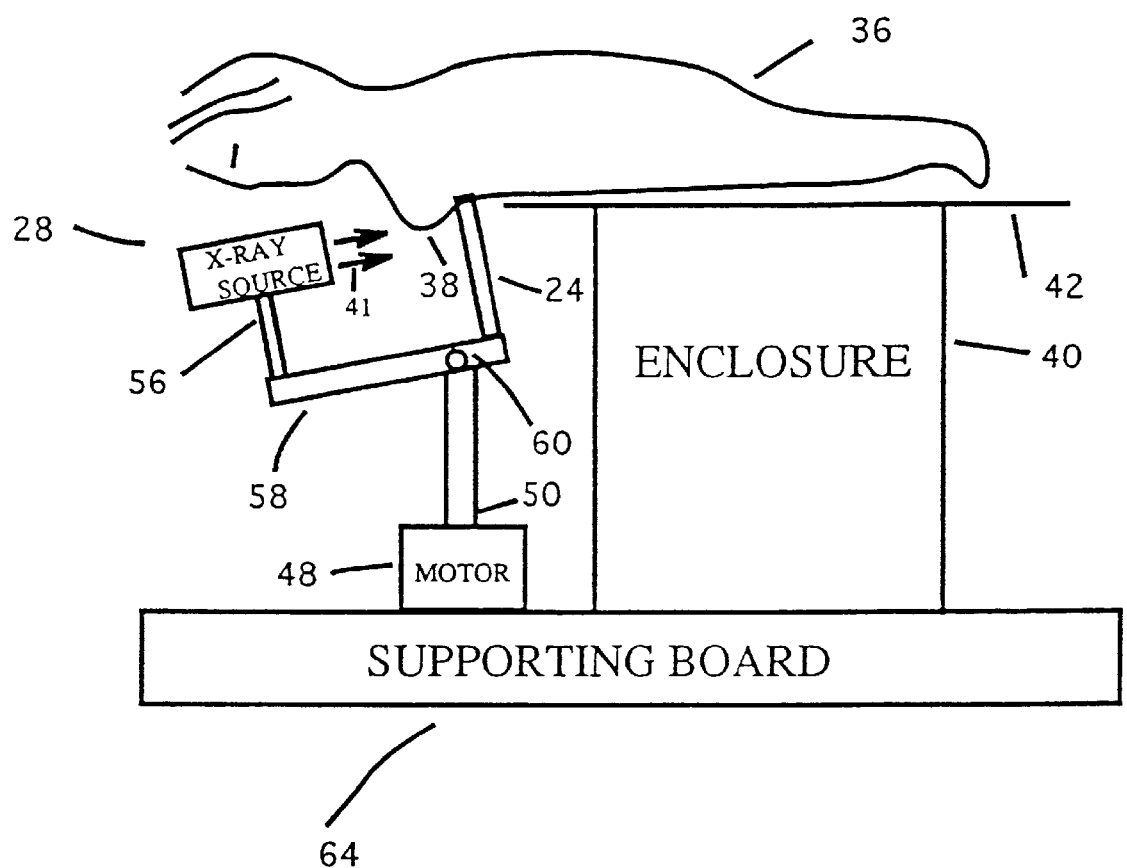
FIG. 9 illustrates a schematic representation of another form of mammography apparatus in accordance with the present invention.

FIG. 9 shows a modification of the machine in FIG. 3. In this case, X-ray source 28 is connected to a connection portion 56 and film table 24 both of which are supported by a supporting plate 58 that is further supported by the rotating shaft 50 and the motor 48 for horizontal rotation. In addition, there is another rotating shaft 60 for oblique movement. The motor 48 and the enclosure 40 are further supported by a supporting board 64. The power supply, computer, and operator console are not shown here for simplicity. In operation, the motor 48 provides different angular images on a horizontal plane, while the rotating shaft 60 provides various oblique images. The net result is that more images are available for more reliable diagnosis. The devices shown in FIG. 3A through 3C are used in this case as well.

Figure 10:
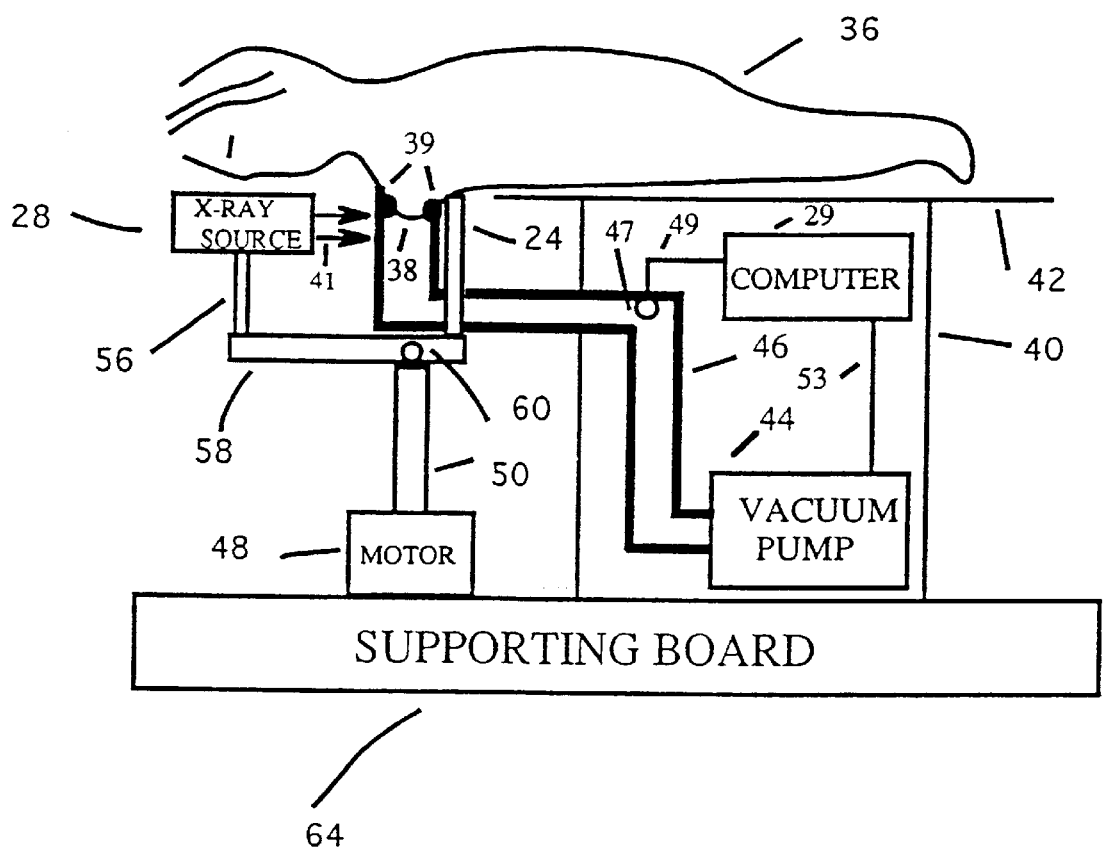
FIG. 10 is a schematic representation of another form of mammography apparatus in accordance with the present invention.
Figure 10A:
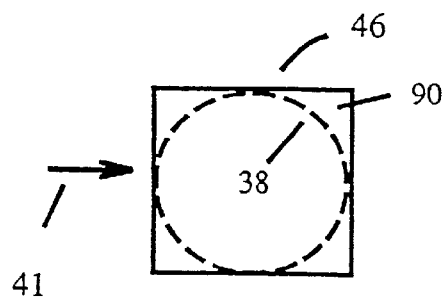
FIG. 10A shows a rectangular cross-section of the tube and the direction of incoming X-ray beams.

FIG. 10 depicts a further modification of the machine in FIG. 9; thus, only different portions are described hereinafter. A vacuum pump 44 is located in an enclosure 40. A tube 46 running through enclosure 40 is positioned between a patient's breast 38 and vacuum pump 44. Tube 46 contains a fluid such as air or water. There is a fluid seal 39 made of a rubber-like material between the breast and the tube end. The tube 46 is made of an X-ray transparent material such as plastic. The inner pressure of the tube 46 is detected by a pressure sensor 47 and controlled by the computer 31 to avoid excess negative pressure. Besides the operation of the machine in FIG. 9, the vacuum pump 44 makes the internal pressure of tube 46 negative compared to the atmospheric pressure. Therefore, breast 38 is further elongated by means of the negative pressure. This further increases the cancer detectability in a wider chest wall area. In case of using water as the fluid in the tube 46, the cross section of the tube is preferably rectangle. FIG. 10A shows a top view of such a rectangular tube 46. X-ray beam 41 runs parallel to the tube wall. Because the total thickness of the breast 38 and the water 90 remains constant in the direction of the X-ray beam radiation, the variation of the beam intensity on the X-ray film surface can be reduced, thus avoiding local overexposure that possibly happens near the nipple position or underexposure that possibly happens near the chest wall position. This is achieved by the fact that the X-ray absorption rate of the breast tissue is nearly the same as that of water. This provides the similar configuration as the water reservoir in FIG. 3.

Figure 11:
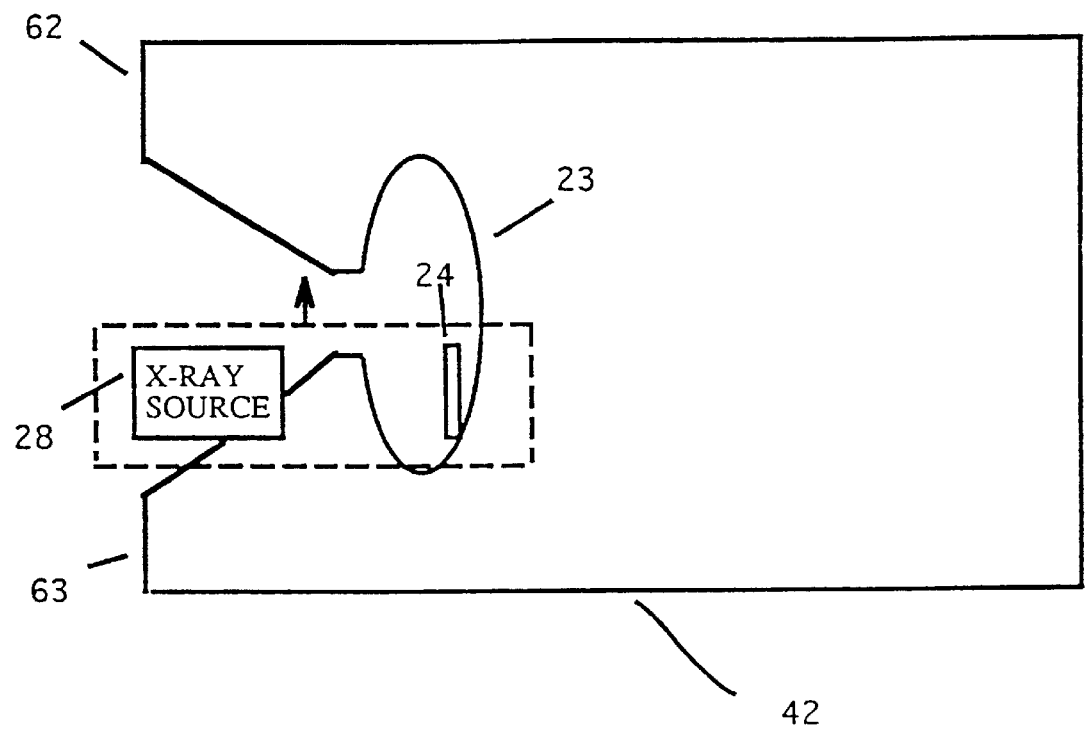
FIG. 11 is a diagram illustrating a bed having a hole or cut area for the breast along with an X-ray source and a film table.

FIG. 11 is a diagram (bottom view) illustrating a bed 42 having a hole or cut area 23 for placing a breast (not shown). An X-ray source 28 and a film table 24 are located under the bed 42. Portions 62 and 63 on bed 42 are for supporting a patient's hands or arms.

Figure 12:
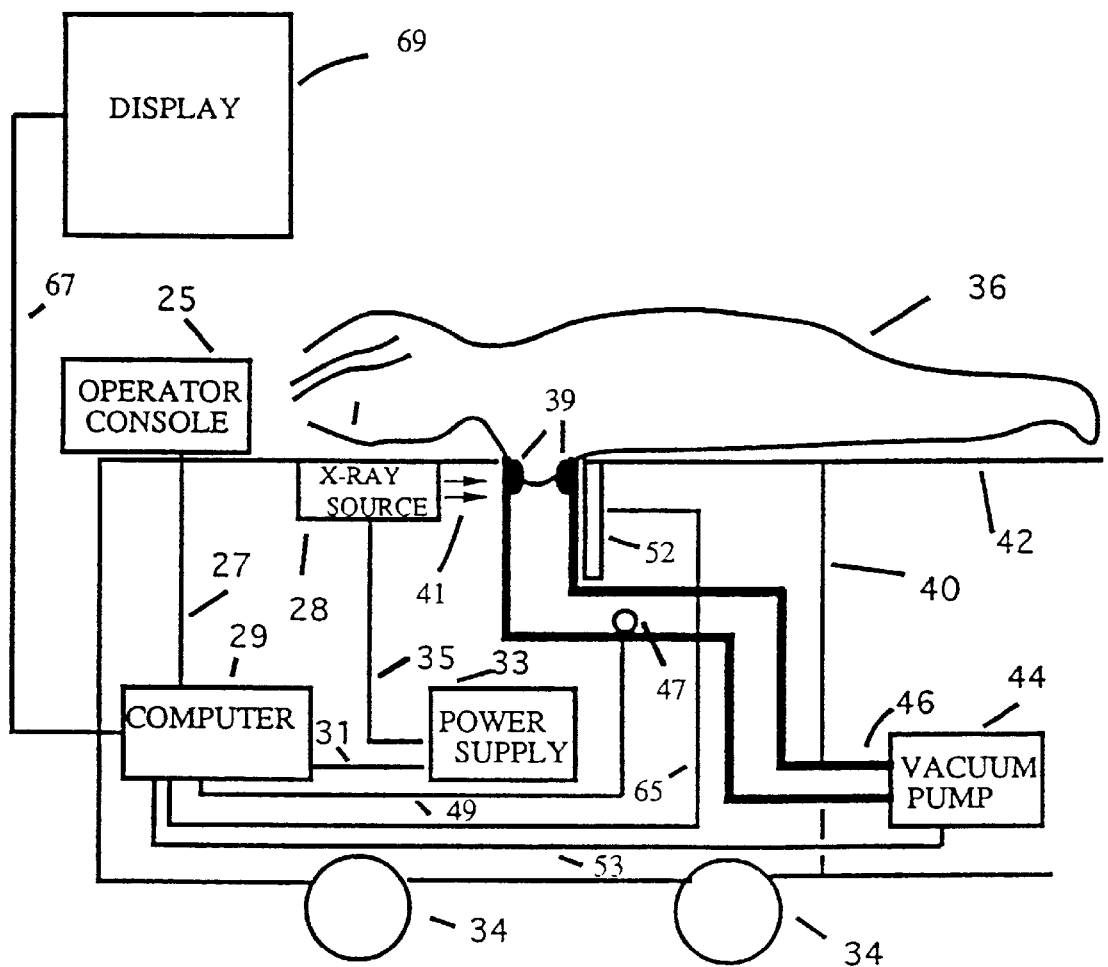
FIG. 12 shows a diagram of still another form of mammography apparatus according to the present invention.

FIG. 12 shows still another modification of the machine shown in FIG. 7, wherein an advanced X-ray detector 52 is used instead of a conventional detector such as an X-ray film, so that the detected X-ray image is electrically transferred to computer 29 through an electric cable 65. Typical advanced X-ray detectors include two-dimensional semiconductor detectors such as CCD (charge coupled detector) or photo diode arrays. Another detector includes "X-ray imaging plates" manufactured by Fuji Film Corporation, Japan with a special photoelectric convertor also available from Fuji Film Corporation. The X-ray imaging plate is a kind of fluorescence plate having image-memorizing capability. With the advanced X-ray detector 52, the X-ray image can be saved electrically in the computer 29 and displayed on a display monitor 69. By watching monitor 69, a medical doctor or an operator can manually adjust the pressure or the position of the receptacle shown in FIG. 7B for the best elongated breast image. Other operations are the same as those described in FIG. 7.

Figure 1:
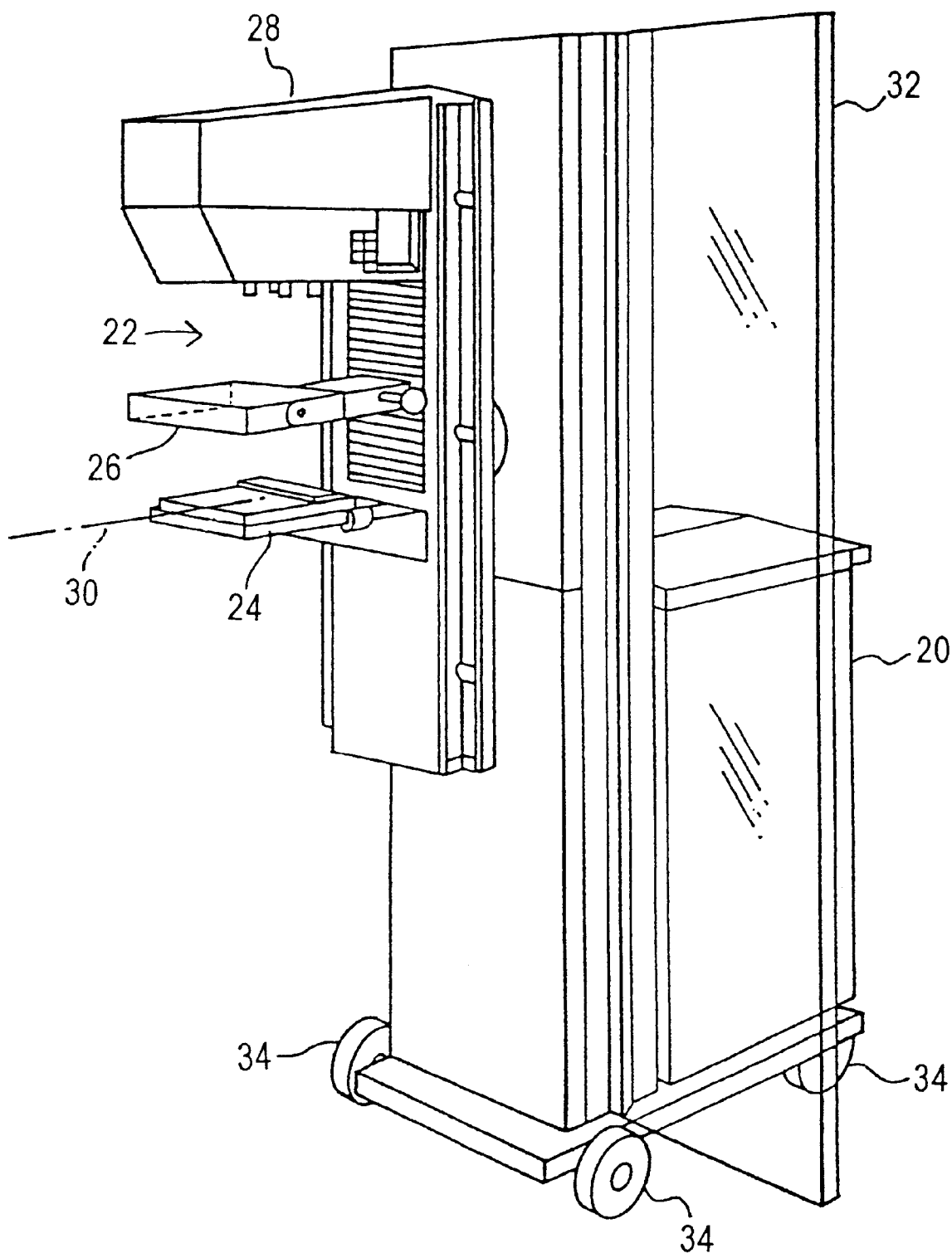
FIG. 1 is a perspective view of a prior art mammography machine.
Figure 2:
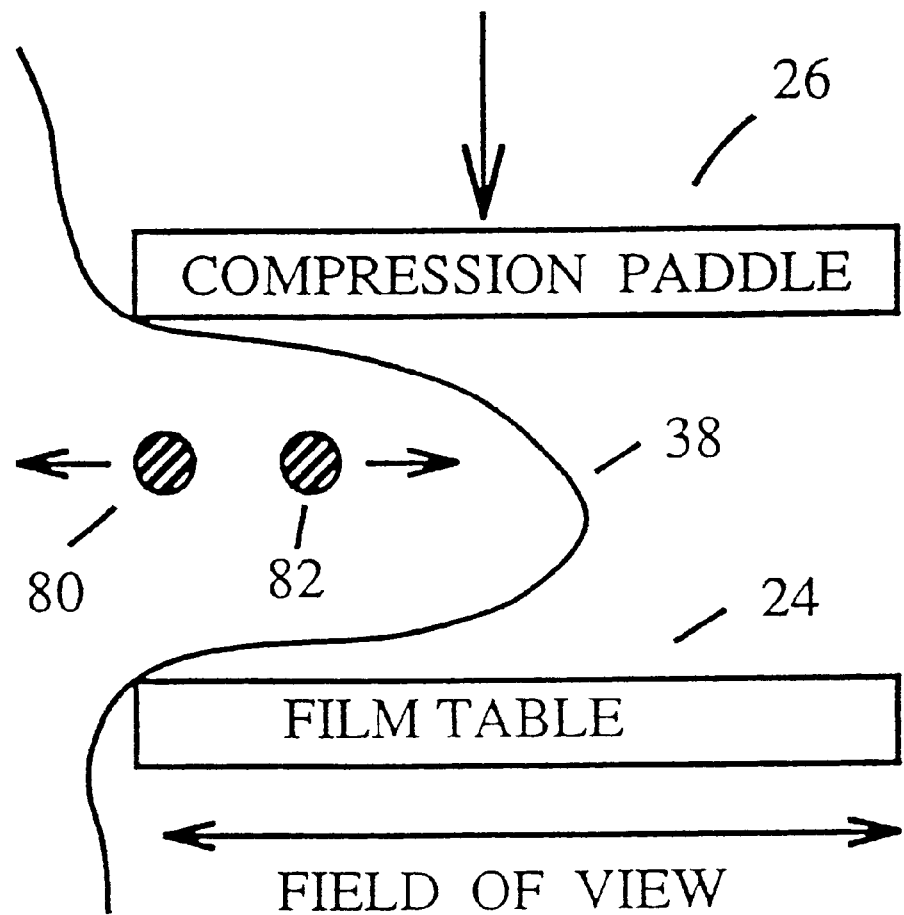
FIG. 2 is a diagram showing a disadvantage of a prior art mammography machine.
Figure 13:
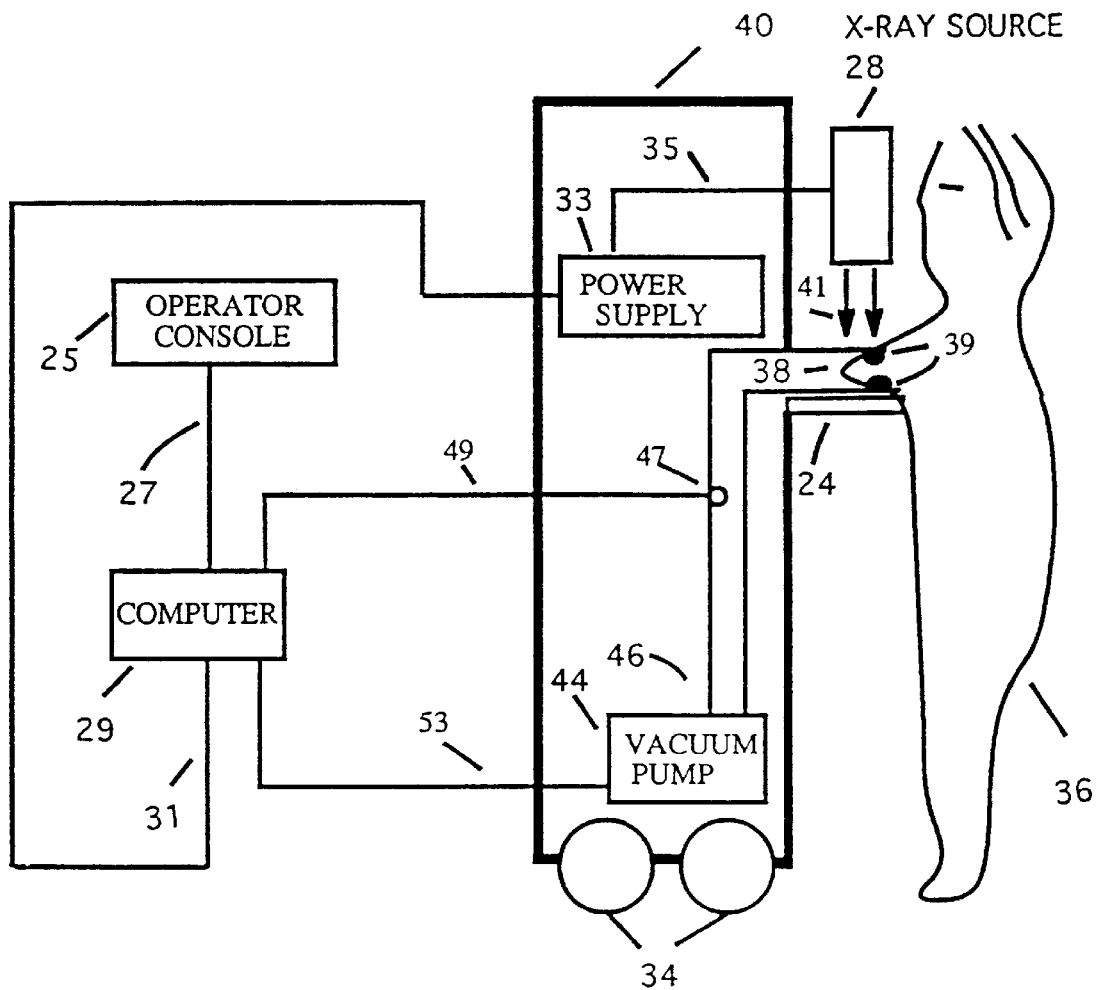
FIGS. 13, 14, and 15 demonstrate still other variations of the present invention.

FIG. 13 shows still another embodiment, wherein only means for elongating the breast by negative pressure is employed. Therefore, a conventional mammography apparatus shown in FIG. 1 can be used with an appropriate modification. In FIG.13, a tube 46 contains a fluid such as air or water. There is a fluid seal 39 made of a rubber-like material between the breast and the tube end. The tube 46 is made of an X-ray transparent material such as plastic. At one end, the tube 46 covers the breast 38 with fluid seal 39. At the other end, the tube 46 is connected to a vacuum pump 44. The breast 38 is elongated when the internal pressure of the tube 46 is made negative compared to the atmospheric pressure by means of vacuum pump 44. Thus even a cancer near the chest wall is imageable on the film 24. In case of using water as the fluid in the tube 46, the cross section of the tube is preferably rectangle. The detailed explanation was mentioned before using FIG. 7C and thus omitted. As a result, the X-ray beam intensity on the film surface is practically uniform. This can avoid local overexposure or underexposure on the film even when using no compression paddle. Other operations are the same as those described in FIG. 1.

Figure 14:
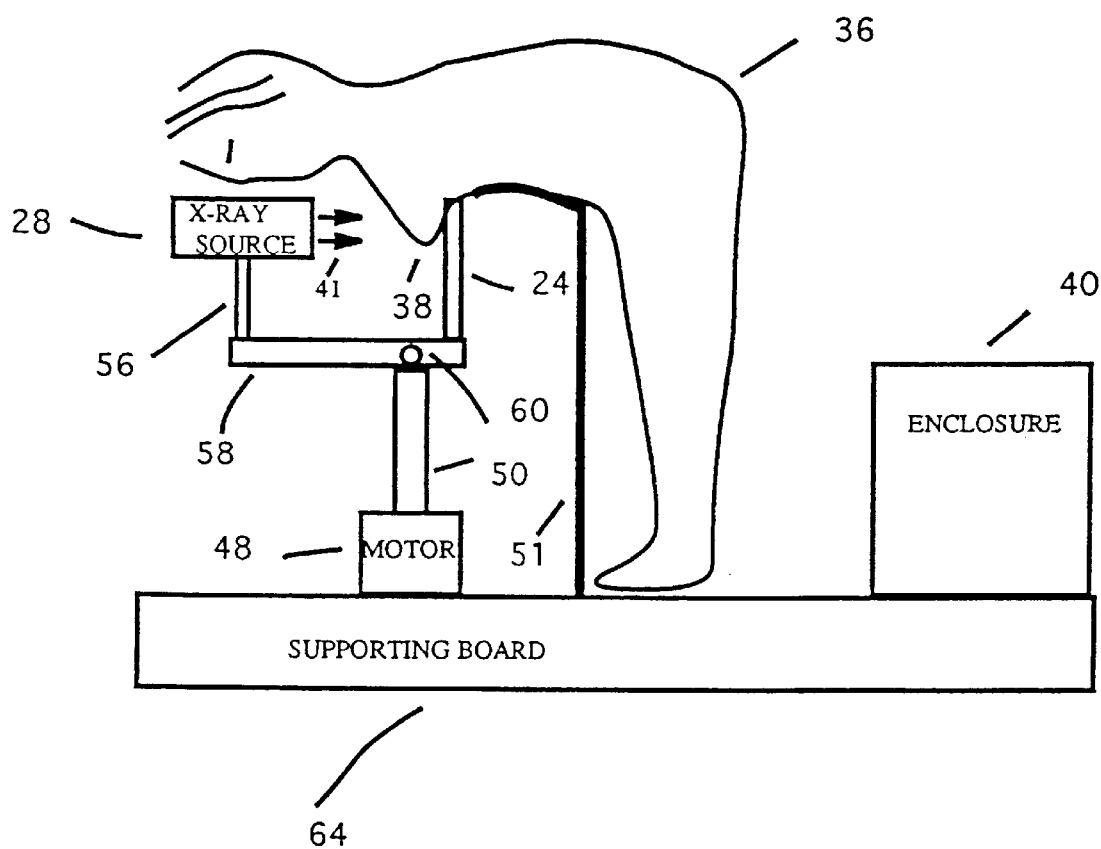

FIG. 14 shows a modification of FIG. 9, wherein only the chest portion of patient 36 is placed in a horizontal direction. Instead of using the bed in FIG. 9, a supporting means 51 for supporting patient abdomen or lower body portion is provided. Operation is substantially the same as that described in FIG. 9. An advantage of this configuration is that the patient can position her breast easily for different angular images.

Figure 15:
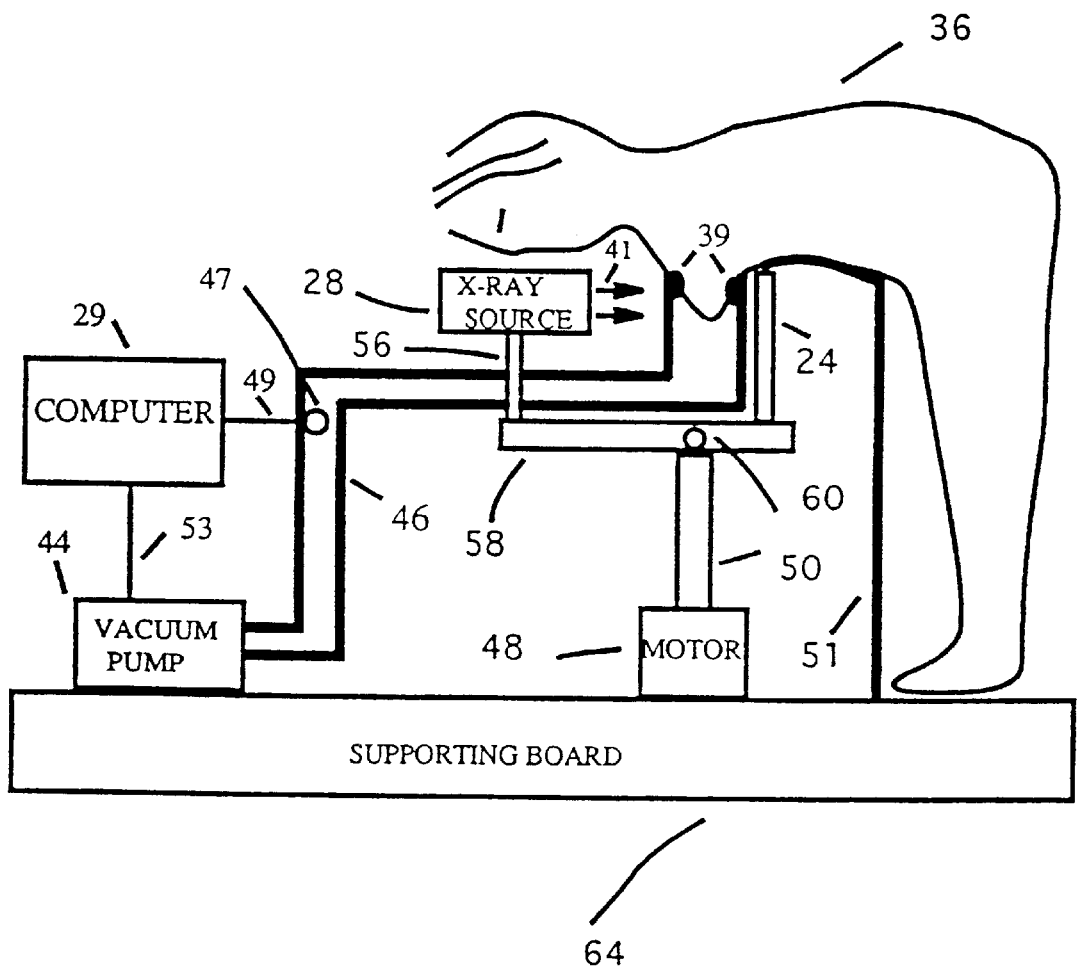

FIG. 15 shows a further modification of FIG. 14, wherein the breast is elongated by a vacuum pump 44. Operation is similar to machines shown in FIGS. 10 and 14 and thus omitted.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A method of examining a breast of a patient comprising the steps of:
    attaching a tube having a rectangular cross-sectional shape to the breast of the patient,
    applying negative pressure to the tube to elongate the breast downward,
    radiating an X ray beam towards the breast so as to direct the beam parallel to a wall of the tube,
    detecting the X-ray beam passed through the breast.

2. The method of claim 1, wherein the patient is supported in a prone position.

3. Apparatus for mammography comprising:
    means for supporting at least a chest of a patient in a horizontal position to elongate a breast of the patient downward due to gravity,
    means for further elongating the breast of the patient downward by using force of suction in addition to the gravity, said elongating means having a bowl shaped receptacle for receiving at least an end portion of the breast, and a vacuum pump for imparting negative pressure to the receptacle;
    means for passing a beam of radiation through the elongated breast; and
    means for detecting a radiation image of the breast.

4. The apparatus of claim 3 further including means for moving the receptacle downward to further elongate the breast.

5. The apparatus of claim 4, wherein said means for moving the receptacle downward is controlled by a computer.

6. Apparatus for X-ray mammography comprising:
    means for supporting at least a chest of a patient in a horizontal position to elongate a breast of the patient downward due to gravity,
    means for further elongating the breast of the patient downward by using force of suction in addition to the gravity, said elongating means having a tube for receiving at least an end portion of the breast, and a vacuum pump for imparting negative pressure to the tube;
    means for generating an X-ray beam to radiate the elongated breast; and
    means for detecting an X-ray image of the breast.

7. The apparatus of claim 6, further comprising a fluid seal made of rubber-like material between the breast and a breast-receiving end of the tube.

8. The apparatus of claim 6, wherein said tube is made of X-ray transparent material.

9. The apparatus of claim 6, wherein said tube contains water.

10. The apparatus of claim 9, wherein said tube has a rectangular cross-section to provide a substantially uniform X-ray beam intensity distribution on a surface of the means for detecting an X-ray image of the breast.

11. A system for examination of at least one breast of a human female, comprising
    a bed for supporting said female in a prone position having a horizontal surface for maintaining said female with said breast down, said horizontal surface being provided with an opening for inserting said breast to elongate said breast due to gravity in a direction perpendicular to said horizontal surface,
    a tube having a first end for receiving said breast, said first end being attached to said opening underneath said horizontal surface,
    a vacuum pump attached to a second end of said tube, for providing in said tube negative pressure in addition to the gravity for further elongating said breast in the direction perpendicular to said horizontal surface,
    an X-ray source for radiating X-ray beams towards said breast inserted into said opening, and
    an X-ray detector for detecting an X-ray image of the breast, said detector having a converter for converting received X-ray radiation into an electrical signal, and a computer coupled to said converter for displaying the X-ray image of the breast,
        wherein said computer stores said X-ray image, and said converter comprises a charge coupled detector.

12. The system of claim 11, wherein said tube is made of X-ray transparent material and has a rectangular cross-section for providing propagation of said X-ray beams in parallel to a wall of said tube.

13. A system for examination of at least one breast of a human female, comprising
    a bed for supporting said female in a prone position having a horizontal surface for maintaining said female with said breast down, said horizontal surface being provided with an opening for inserting said breast to elongate said breast due to gravity in a direction perpendicular to said horizontal surface,
    a tube having a first end for receiving said breast, said first end being attached to said opening underneath said horizontal surface,
    a vacuum pump attached to a second end of said tube, for providing in said tube negative pressure in addition to the gravity for further elongating said breast in the direction perpendicular to said horizontal surface,
    an X-ray source for radiating x-ray beams towards said breast inserted into said opening, and
    an X-ray detector for detecting an X-ray image of the breast, said detector having a converter for converting received X-ray radiation into an electrical signal, and a computer coupled to said converter for displaying the X-ray image of the breast,
        wherein said converter comprises a fluorescence plate having image-memorizing capability.

* * * * *